United States Patent [19]

Walter et al.

[11] Patent Number: 4,950,545

[45] Date of Patent: Aug. 21, 1990

[54] MULTIFUNCTIONAL FACIAL TISSUE

[75] Inventors: Rebecca S. Walter; Paulette M. Rosch, both of Appleton, Wis.; David N. Haney, San Diego, Calif.

[73] Assignee: Kimberly-Clark Corporation, Neenah, Wis.

[21] Appl. No.: 316,048

[22] Filed: Feb. 24, 1989

[51] Int. Cl.⁵ .................. B32B 27/00; B32B 9/04; D04H 1/00
[52] U.S. Cl. .................................. 428/446; 428/198; 428/211; 428/290; 428/449; 428/452
[58] Field of Search ............... 428/198, 211, 449, 452, 428/290, 446

[56] References Cited

U.S. PATENT DOCUMENTS

| | | | |
|---|---|---|---|
| 3,814,096 | 6/1974 | Weiss et al. | 128/260 |
| 3,818,533 | 6/1974 | Scheuer | 15/104.93 |
| 4,112,167 | 9/1978 | Dake et al. | 428/154 |
| 4,355,021 | 10/1982 | Mahl et al. | 424/443 |
| 4,395,454 | 7/1983 | Baldwin | 428/290 |
| 4,469,840 | 9/1984 | Alberts et al. | 524/500 |
| 4,481,243 | 11/1984 | Allen | 428/154 |
| 4,513,051 | 4/1985 | Lavash | 428/212 |

Primary Examiner—Ellis P. Robinson
Assistant Examiner—Amy Hulina
Attorney, Agent, or Firm—Gregory E. Croft

[57] ABSTRACT

Facial tissues containing a silicone compound exhibit improved softness, and reduced lint while maintaining absorbency. At the same time, the tissues of this invention do not smear glass as is the case with commercially available lotion-treated tissues.

4 Claims, 1 Drawing Sheet

MULTIFUNCTIONAL FACIAL TISSUE

BACKGROUND OF THE INVENTION

Facial tissues are used by the consumer for a wide variety of applications. Everyday uses include nose care, eyeglass cleaning, cosmetic removal and household wipe-ups, etc. Each type of use requires different attributes from the tissue. Nose care, for example, requires a soft tissue which will not irritate sensitive skin. Absorbency is especially important for wiping up liquids. Cleaning eye glasses requires a non-smearing and low-linting tissue. In an effort to satisfy the needs of users having a cold, one tissue manufacturer is marketing a facial tissue which is treated with an emollient or lotion to lessen the effects of the tissue on an irritated nose. Unfortunately, such a product does not meet the needs for other types of uses, such as cleaning eye glasses, because it leaves an oily residue on the face and hands of the user and smears glass surfaces.

Therefore there is a need for a soft facial tissue which is multifunctional, i.e. it performs well for all tissue uses, including eye glass cleaning, as well as being soft enough for nose care.

SUMMARY OF THE INVENTION

It has now been discovered that a facial tissue can offer the same softness of a lotion-treated tissue while retaining other multi-functional characteristics such as absorbency, strength, not smearing glass and not leaving an oily residue on the user's hands and face. These benefits are accomplished by incorporating a silicone compound into a facial tissue at low levels. Surprisingly, despite the low add-on level, the silicone compounds impart improved softness to the tissue while maintaining absorbency and strength. In addition, the linting of the tissue is significantly reduced and the tissue will not significantly smear glass so that the tissue can be used to wipe eye glasses.

Hence in one aspect the invention resides in a tissue product, such as a facial tissue, comprising one or more tissue sheets or plies, said tissue product containing from about 0.1 to about 5 weight percent solids of a silicone compound. Preferably, the silicone compound-containing tissue exhibits a Smear Index (hereinafter defined) of less than 1.0. In addition, it is preferred that the facial tissue have a Lint Reduction Index of about 5 or more. Furthermore, the presence of the silicone compound advantageously increases the Sink Time, a measure of absorbency and hereinafter defined, no more than about 30 seconds relative to the untreated base sheet, preferably no more than about 10 seconds, and most preferably no more than about 5 seconds.

For purposes herein, "tissue sheet" is a single ply sheet suitable for facial tissue or bath tissue use having a density of from about 0.1 grams per cubic centimeter to about 0.3 grams per cubic centimeter and a basis weight of from about 4 to about 40 pounds per 2880 square feet. Tensile strengths in the machine direction are in the range of from about 100 to about 5,000 grams per inch of width. Tensile strengths in the cross-machine direction are in the range of from about 50 to about 2500 grams per inch of width. Creped cellulosic tissue sheets of paper-making fibers are preferred, although synthetic fibers can be present in significant amounts. Tissue sheets can be layered or blended.

Suitable silicone compounds are those silicone compounds which provide a smooth, lubricated surface feel, preferably without smearing glass as described herein. Preferably the silicone compounds are present in an aqueous emulsion and/or solution for ease in handling and processing. A wide variety of such silicone compounds are known in the art. Specific suitable silicone compositions include, without limitation, polydimethyl siloxanes; mixtures of polydimethyl siloxanes and alkylene oxide-modified polydimethyl siloxanes; organomodified polysiloxanes; mixtures of cylic- and non-cylic-modified dimethyl siloxane; and the like. Number average molecular weights are generally about 10,000 or greater. Also suitable are aqueous mixtures of tetraethoxy silane, dimethyl diethoxy silane, and ethylene oxide/dimethyl siloxane copolymer. A preferred composition contains about 5 weight percent tetraethoxy silane, about 5 weight percent dimethyl diethoxy silane, and about 2 weight percent ethylene oxide/dimethyl siloxane copolymer in water. In such silane mixtures, the ethylene oxide-dimethyl siloxane acts as a coupling agent to bind the silicone to the tissue sheet surface, thus retarding residue build-up on the contact surface and thereby reducing the greasy feeling associated with some lubricants.

The amount of silicone solids in the tissue sheet can be from about 0.1 to about 5 weight percent, based on the finished basis weight of the tissue sheet. Preferably the amount of the silicone compound is from about 0.5 to about 3 weight percent and most preferably from about 0.7 to about 2 weight percent. Amounts below 0.1 weight percent provide little benefit to the facial tissue in terms of softness improvement. Amounts above 5 weight percent show little or no improvement in softness over the lesser amounts and may become economically unattractive. The silicone compound can be incorporated into the facial tissue by any suitable means, including printing, spraying, dipping and the like. The silicone compound can be incorporated into the tissue sheet at any point in the tissue manufacturing process from the wet end to the converting process. Preferably the silicone compound is printed onto a dried, creped tissue sheet between the base sheet manufacturing process and the final tissue product converting process. Printing provides precise control of the add-on amount of the silicone compound and places the silicone compound on the surface of the tissue where it is most effective. In addition, printing provides a distinct pattern of treated areas and untreated areas, thereby mitigating any decrease in absorbency attributable to the presence of silicone compounds which are generally regarded as hydrophobic.

As used herein, "Sink Time" is related to absorbency and is the time it takes for a given sample to completely wet out when placed in water. More specifically, absorbency is determined by cutting 40 sheets or plies of the tissue sample into 2.5 inch squares. The 40 square sheets are stacked together and stapled at each corner to form a pad. The pad is held close to the surface of a constant temperature water bath (30° C.), which is at least 4 inches deep, and dropped flat onto the water surface, staple points down. The time taken for the pad to become completely wetted, measured in seconds, is the Sink Time for the sample and represents the absorbent rate of the tissue. Increases in Sink Time represent a decrease in absorbent rate.

As used herein, the "Lint Reduction Index" is a measure which reflects the decrease in the amount of lint seen by the consumer as compared to an untreated tissue. The Lint Reduction Index is hereinafter described in detail with reference to the Drawing.

As used herein, the "Smear Index" is a measure of the amount of smearing a tissue will cause upon rubbing a glass slide under controlled conditions, hereinafter described with reference to the Drawing. It reflects the amount of smearing a consumer can expect when using a tissue to wipe eye glasses or other smooth surfaces, such as glass table tops and the like.

DETAILED DESCRIPTION OF THE DRAWING

Figure 1:
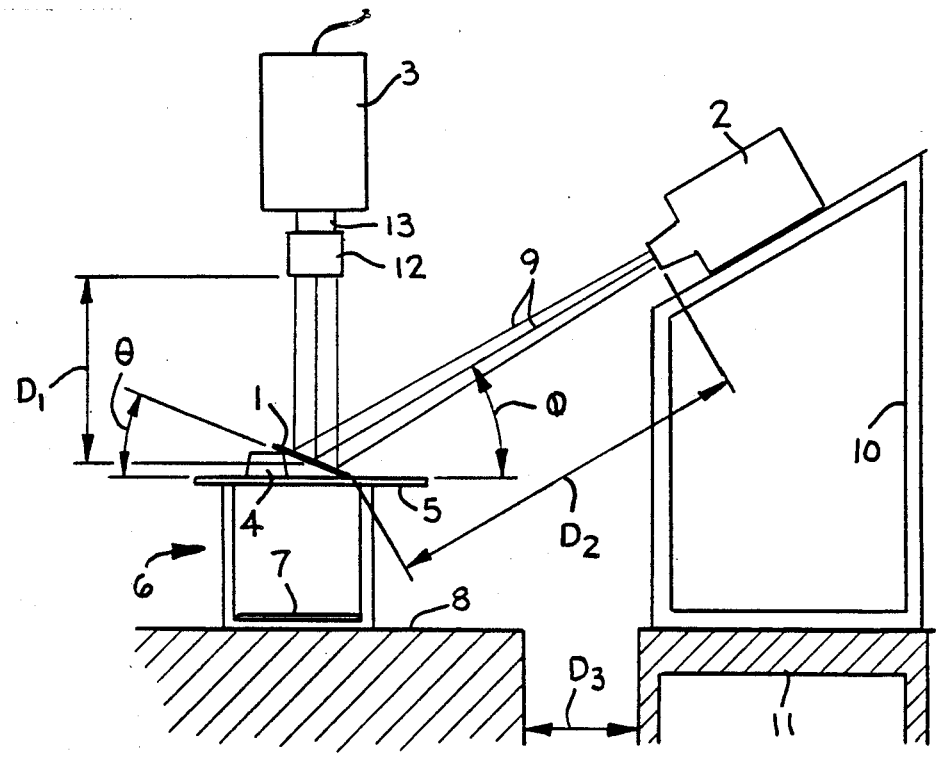
FIG. 1 is a schematic representation of the apparatus used to determine the Smear Index.

Referring to FIG. 1, the apparatus and method for determining the Smear Index will be described in detail. In general, the method involves testing a sample glass slide 1 which has been controllably rubbed with a test tissue sample to create a smear. With all room lights off, the glass slide is illuminated with a slide projector 2 and the reflected light is detected by a "TV" camera 3. The image detected by the TV camera is then processed by an image analysis system (not shown) to yield a Smear Index number, which is a brightness value between 0 and 63 (a 64 value gray scale). The apparatus shown herein is intended to provide angled darkfield imaging which is just short of specular reflection.

More specifically, the glass slide is a pre-cleaned glass micro slide, $75 \times 50$ $mm$, plain, thickness of 0.96 to 1.06 $mm$., No. 2947 available from Corning Glass Works, Scientific Glassware Department, Corning, N.Y. 14830. Each slide, prior to being smeared, is thoroughly washed in a dilute cleaning solution of 10 ml. MICRO® laboratory cleaning solution (available from International Products Corporation, Trenton, N.J.) and 700 ml. water. A firm rubbing motion using a sponge, wash cloth, or similar material is used. The slides are then rinsed in deionized water. Each slide is then dipped into a warm solution of potassium hydroxide (10 pellets) and ethanol (600 ml.) for about 10 seconds and rinsed with deionized water. The rinsed slides are further rinsed with filtered deionized water and allowed to dry, vertically, in a dust-free environment. When dry, the slides are ready for use and are stored in a dust-free container. Rubber gloves should be worn throughout the slide preparation and smearing process, since any stray marks on the slide will affect final test results.

To place smears on the slides for testing, the cleaned slides are placed on a clean, lint-free surface. A 2 inch by 3 inch metal template, having a one inch diameter hole in the center, is placed over the slide. A 2 inch by 2 inch piece of tissue sample to be tested is placed over the hole in the template. The narrow end (⅞ inch diameter) of a #5½ rubber stopper is placed over the hole in the template resting on top of the tissue sample. A 5 pound weight is balanced on top of the rubber stopper and allowed to stand for 3 minutes. This causes the tissue sample to be pressed onto the glass slide through the hole in the template by the weighted rubber stopper. After 3 minutes, the rubber stopper and 5 pound weight are turned together 180° clockwise and then 180° counter-clockwise. Care is taken not to exert any additional downward force. The weight, stopper, sample and template are lifted off the slide, in that order. The resulting smeared slide should be tested for a Smear Index within 10 hours.

Referring again to FIG. 1, dust-free or low dust environments are essential and the smeared sample slides are de-dusted with compressed gas prior to being tested. The sample slide is then placed at an angle $\theta$ of about 20° from horizontal using a black rubber stopper 4 as a support. The working distance $D_1$ between the smear region on the slide and the bottom of the TV camera lens is about 17.5–18 cm. The sample slide and rubber stopper are supported on a ¼ inch thick piece of plate glass 5 which in turn rests on a negative developer box 6 (Kodak $4 \times 5$ Hard Rubber Tank). A piece of flat black construction paper 7 is placed in the bottom of the box, which serves as a Planck absorber (light trap). The light trap and TV camera are supported by a macroviewer stand 8. The particular macroviewer stand used is a Cambridge Instruments Macroviewer with an automacrostage feature. However, any stand which can securely support the sample and necessary hardware can be used, including an Eberhardt Macroviewer, parts nos. 401015, 701000, and 701020 (Eberhardt Instrument Company, Downers Grove, Ill.).

The sample slide is illuminated by a 300-watt beam at infinity focus using a Bell and Howell slide projector, Design 859B. A 5 mm. circular piece of black rubber-coated photo darkroom cloth is placed on the sample slide next to the left side of the smear. This acts as a "reflectance object" for scanner control to allow white level to be set at exactly 1.00 volt. The center of the projection beam 9 makes about a 28°–30° angle $\phi$ with respect to horizontal, at a distance $D_2$ of about 70 cm. The slide projector is supported by a Plexiglass® rack 10 having a movable table top to allow various height and angle adjustments. The rack is supported on a separate table 11 positioned a distance $D_3$ of about 12 inches from the macroviewer stand 8.

The TV camera 3 is a Quantimet 900 Newvicon Scanner coupled with a 50 mm. EL-NIKKOR 1.28 enlarging lens 12 using a 5 mm. C-mount extension tube 13 and F-to-C adapter. The lens and adapter are available from Nikon Instruments/OEM Sales Group, Garden City, N.Y. The extension tube is available from Dapple Systems, Sunnyvale, Calif. The aperture used was f/5.6, but other aperture settings can be used to ensure that the entire smear image remains in focus. Other cameras which can be used are those possessing a nearly linear "gamma" (linear signal response).

Any modern image analysis system would be able to enact the sequence of steps necessary to process the smear image delivered by the apparatus described above. Suitable image analysis systems include the Cambridge Quantiment 970®, Zeiss/Kontron IBAS®, Joyce-Loebl Magiscan®, Leitz TAS®, Olympus CUE 2/4, and others. An important requirement is sufficient spacial resolution with a minimum of $512 \times 512$ pixels. The particular image analysis system used to generate the data presented herein was the Quantimet 900. The steps are as follows:

1. Enter Specimen identity.
2. Adjust scanner manual gain, use autogain, or control illumination with a variable voltage transformer to produce optimum scanner response (here, white level =1.00 volt). (For those image analysis systems that do not inherently record scanner white level, a separate photo-detector and meter can be used. Alternatively, an oscilloscope tap into the scanner can be used to record voltage directly.)

3. Set shading correction or background subtraction to correct for glare and vignetting in optics, spatial non-linearity in the scanner, and other effects.

4. Calibrate the system in centimeters, or load from disk a previously saved calibration factor.

5. Define image arrays for storing gray or binary images, if not the default condition already.

6. Either acquire a gray image or detect the wipe smear spot as a binary image, if possible, or detect entire frame if edit commands will be needed to encircle an undetectable wipe-smear region.

7. Use light-pen or "mouse" editing to just barely encircle the wipe-smear, unless direct detection was possible in step 6 above.

8. Position a circular frame around the detected or encircled wipe-smear to exclude image artifacts that may occur elsewhere in the field-of-view.

9. Amend the binary image with 3 steps of dilation followed by 3 steps of erosion (3 "closing" operations).

10. Amend the binary image with 3 steps of erosion following by 3 steps of dilation (3 "opening" operations).

11. Fill any holes in the binary image.

12. Using the binary image, measure its area and perimeter, although the latter was not of primary importance here.

13. Using the binary image as a mask overlayed upon the original gray image, measure the optical brightness of only that portion of the gray image hidden under the binary image. Divide this total optical brightness [$\Sigma(B \times P)i$] by the total number of pixels in a binary [$\Sigma(P)i$] to get average smear brightness.

14. Record by printout or monitor display:
    (a) White level actually developed for the analysis by scattered light from the smear and reflectance object (should be 1.00);
    (b) average smear brightness as defined above.

15. Calculate: the difference between brightness values for sample slides and mean brightness from a set of blank slides that have no smears.
These then represent the final data from this analysis, which are taken from 10 individual sample slides for a single type of additive on tissues, and then averaged for the group. The average is the Smear Index.

Figure 2:
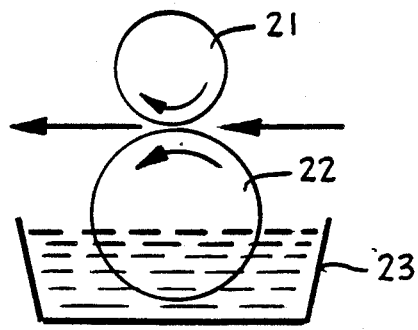
FIG. 2 is a schematic representation of the apparatus used to determine the Lint Reduction Index.

Referring now to FIG. 2, the apparatus for determining the Lint Reduction Index will be described in detail. The Lint Reduction Index is determined using a GFL Fluff Tester, Model No. SE 56, manufactured by Lorentzen and Wettre, Stockholm, Sweden. The operation of the device is generally as illustrated in FIG. 2. More specifically, 15 tissues for each sample of tissue to be tested, each tissue C-folded or V-folded to measure about 4½ inches by about 9¼ inches, are passed through a nip between two rolls with the longer side parallel to the rolls. The top roll 21 is a 40 mm. diameter rubber roll, 180 mm. in length. The bottom roll 22 is a steel roll, 92 mm. in diameter and 190 mm. in length. The linear nip pressure is 490 N/m roll width. Peripheral speed is 0.4 m/sec. The steel roll is partially submersed in the tray 23 of water containing 250 ml. of water. As the tissue sample is inserted into the device, a cam action lowers the rubber roll against the steel roll and the sample is pulled between the rolls. Lint from the sample is transferred to the steel roll, which is moistened in the water bath. Surplus water is removed by a doctor while the roll is rotating. The remaining moisture is determined by the grain of the steel roll and the peripheral speed. The lint is washed off as the surface of the steel roll enters the water again and the lint is recovered in the water tray. The lint-containing water is then transferred to a clean sample jar and analyzed for particle count using a Kajaani FS 100 fiber analyzer. However, any means for counting the number of fiber particles contained in the solution can be used, including filtering the solution and counting the fibers manually under a microscope. Clearly, however, the Kajaani FS 100 instrument is more convenient. Two 5 ml. samples are analyzed from each 250 ml. test sample. This procedure of putting 15 tissues through the GFL Fluff Tester and analyzing two 5 ml. samples for particle count is repeated a total of twenty times. The particle count numbers are added together and divided by the number of tests (40). The resulting average is the lint count for the tissue sample. The lint count for the treated tissue sample is compared to the lint count for an untreated control tissue of the same base sheet. The Lint Reduction Index is calculated according to the following formula:

$$\text{Lint Reduction Index} = \frac{(c - t)}{c} \times 100$$

wherein
 c = average particle count for the control tissue; and
 t = average particle count for the treated tissue.

EXAMPLES

EXAMPLES 1: PREPARATION OF SILICONE-TREATED FACIAL TISSUE

A two-ply silicone-treated facial tissue in accordance with this invention was prepared by printing a silicone compound onto the outer surfaces of the tissue. More specifically, two rolls of single-ply facial grade creped tissue, each ply having a basis weight of 9.4 pounds per 2880 square feet and consisting of a blend of 35 weight percent softwood fibers and 65 weight percent hardwood fibers, were unwound and crimped together at a speed of about 700 feet per minute. The resulting two-ply base sheet was then treated with a silicone compound on both sides using a rotogravure printer, first printing on one side and then the other. The silicone-treated sheet was then slit and converted into boxed facial tissues without additional drying.

The particular rotogravure printer used was an Arrow Converting Equipment Company press. The printing pattern was a uniformly overall pattern provided by printing cells of 54 micron size spaced apart by 10 microns. The add-on amount of the silicone compound was about 1–2 weight percent, based on the air dry weight of the two-ply base sheet. The add-on amount can vary, of course, depending on the printing cell size and the viscosity of the silicone compound. The particular silicone compound used was an aqueous emulsion of an organo-modified polysiloxane manufactured by Union Carbide, designated as Y-12224. The resulting tissue was soft, absorbent, low-linting, and non-smearing.

EXAMPLE 2: IMPROVED SOFTNESS OF SILICONE-TREATED TISSUES

In order to illustrate the softness improvement attributed to the presence of a silicone compound, a three-ply silicone-treated tissue was prepared in a manner similar to that described in Example 1. As a control, a three-ply facial tissue was made with the same base sheet, but not treated with the silicone compound. Each ply of the tissue samples had a basis weight of 7.8 pounds per 2880 square feet and consisted of 35 weight percent softwood fibers and 65 weight percent hardwood fibers. The silicone-treated product contained about 0.97 weight percent of silicone compound solids (Y-12224 from Union Carbide, Tarrytown, N.Y.) on the outside plies. Both samples were submitted to a trained sensory panel of ten persons who numerically evaluated (0–60 scale) the two samples for different attributes. Except for abrasiveness, higher numbers mean greater softness. The results, which are statistically significant at the 95 percent confidence level, are set forth in Table 1 below:

TABLE 1

| | (Softness) | |
|---|---|---|
| | Control | Silicone-Treated |
| Abrasiveness | 20.48 | 16.80 |
| Smoothness | 40.18 | 44.40 |
| Pliabilty | 36.80 | 42.00 |
| Gentle on face | 33.53 | 41.45 |

No significant differences were found between the control and the silicone-treated sample for absorbency, cushioniness, volume, and durability. These results clearly show an improvement in overall perceived softness and comfort attributable to the silicone-treatment. It is believed that the perceived softness for any base sheet can be improved by the silicone treatment, but the level of softness is also largely dependent upon the softness in the base sheet. Similar results have been achieved with other silicone compositions, including Union Carbide Y-12225, Y-12226, which are mixtures of polydimethyl siloxanes and alkylene oxide-modified polydimethyl siloxanes, and Wacker Silicone E-678 (Adrian, Mich.), which is an aqueous emulsion of a 15–40 percent mixture of non-cyclic polydimethyl siloxane components with molecular weights between 100,000–400,000 and a 20–60 percent mixture of cyclic demethyl siloxane components with the -Si-O- ring units numbering between 3 and 9.

EXAMPLE 3: LINT REDUCTION

Facial tissue having three plies, each ply having a basis weight of about 8.9 pounds per 2880 square feet and containing about 35 weight percent softwood fibers and 65 weight percent hardwood fibers, were tested for Lint Reduction Index as previously described. Three different tissue samples were tested: a control which was untreated, but which was subjected to the same manipulations as a treated sample undergoes during the silicone printing process; Sample No. 1 in which the two outer plies were printed with about 1.72 weight percent of a silicone compound (E-678 from Wacker Silicones); and Sample No. 2 in which the two outer plies were printed with about 1.9 weight percent of a different silicone compound (Y-12225 from Union Carbide). The results of the test are set forth in Table 2.

TABLE 2

| | (Lint Reduction) | |
|---|---|---|
| | Average Lint Count | Lint Reduction Index |
| Control | 2825 | — |
| Sample 1 | 2021 | 28.5 |
| Sample 2 | 2017 | 28.6 |

These results illustrate that the silicone-treatment substantially reduces linting relative to an untreated base sheet.

EXAMPLE 4: ABSORBENCY

In order to illustrate the effect of the silicone-treatment on the absorbency of the tissue, two-ply silicone-treated facial tissues as described in Example 1 were prepared along with two different untreated control tissues. The absorbency test described above was conducted three times for each sample and the results are summarized in Table 3.

TABLE 3

| (Absorbency) | |
|---|---|
| | Sink Time (seconds) |
| Control #1 | 1.32 |
| Silicone-Treated (Wacker E-678) | 2.98 |
| Control #2 | 1.95 |
| Silicone-Treated (Union Carbide Y-12224) | 3.81 |
| Silicone-Treated (Union Carbide Y-12225) | 4.61 |
| Silicone-Treated (Union Carbide Y-12226) | 4.10 |

The results show that although the silicone-treated sample had a slower absorbent rate (longer Sink Times), the difference is not significant in that the Sink Time is only on the order of 1–2 seconds longer. This difference would be undetectable in a normal use situation, where Sink Times of up to 40 seconds for other types of tissues have not been detected by consumers.

EXAMPLE 5: SMEARING GLASS

In order to illustrate the advantageous use of a silicone-treated tissue for contacting glass surfaces, two different three-ply silicone-treated facial tissues were prepared as described in Example 1. Sample #1 was treated with 1.2 weight percent Union Carbide Y-12224 silicone compound. Sample #2 was treated with 1.7 weight percent Wacker Silicones E-678. Sample #3 was a commercially available lotion-treated facial tissue (PUFFS PLUS ®). All three samples (five samples each) were tested for Smear Index. The results are set forth in Table 4.

TABLE 4

| (Smear Index) | |
|---|---|
| Sample | Smear Index |
| #1 | 0.50 |
| #2 | 0.31 |
| #3 | 17.2 |

These results clearly show a remarkable improvement relative to the commercially-available product for reducing smearing. Hence the silicone-treated facial tissues are not limited in their functionality by objectionable smearing characteristics.

The foregoing examples, given for purposes of illustration, are not intended to limit the scope of this invention, which is defined by the following claims.

We claim:

1. A facial tissue comprising at least two tissue sheets, said facial tissue containing from about 0.1 to about 5 weight percent solids, based on the finished basis weight of the tissue sheets, of a silicone compound having a number average molecular weight of about 10,000 or greater and which is incorporated into the tissue with an aqueous carrier, said tissue having a Smear Index of 1.0 or less, a Lint Reduction Index of 5 or greater, and a Sink Time no more than 30 seconds greater than the Sink Time of the same facial tissue without the silicone compound.

2. The tissue of claim 1 wherein the Sink Time is no more than 10 seconds greater than the Sink Time of the same tissue without the silicone compound.

3. The tissue of claim 1 wherein the Sink Time is no more than five seconds greater than the Sink Time of the same tissue without the silicone compound.

4. The tissue of claim 1 consisting of three tissue sheets or plies, wherein both outer sheets or plies contain a silicone compound.

* * * * *